Figure 1:
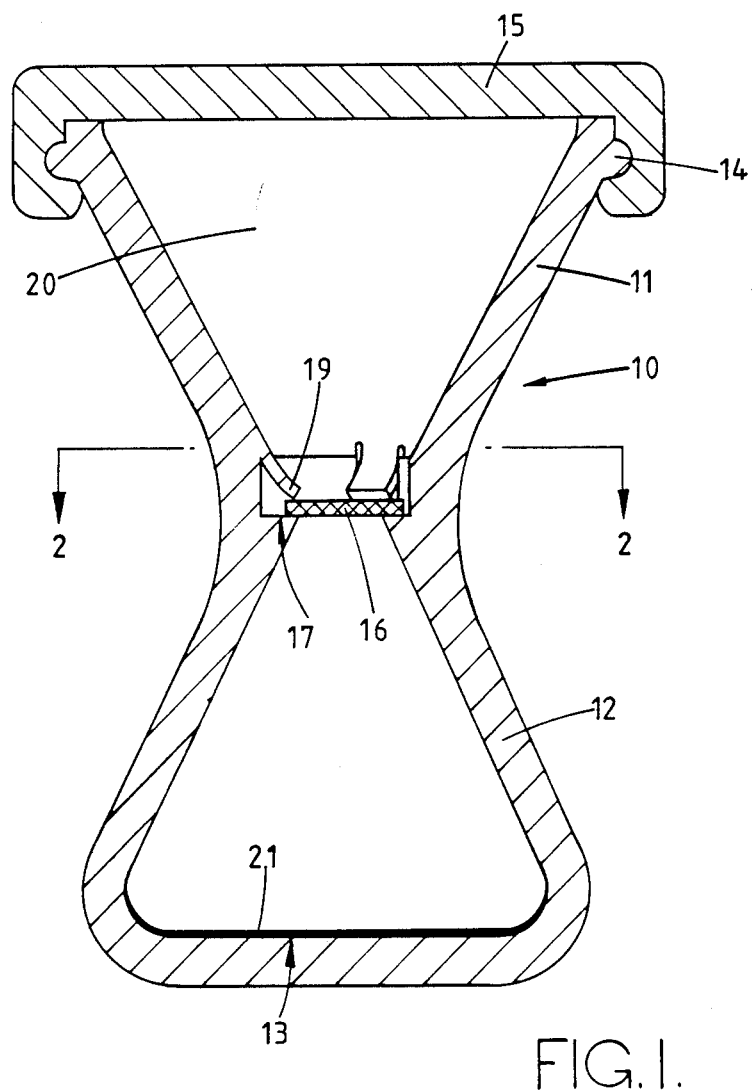

United States Patent [19]

Skinner et al.

[11] Patent Number: 4,857,463
[45] Date of Patent: Aug. 15, 1989

[54] METHOD OF PREPARING INTRACELLULAR PARASITES FOR STORAGE

[75] Inventors: Gordon R. B. Skinner, Dorridge; Alexander Buchan, Birmingham, both of England

[73] Assignee: Medical Research International Ltd., Dorridge, England

[21] Appl. No.: 39,015

[22] Filed: Apr. 16, 1987

[30] Foreign Application Priority Data

Apr. 19, 1986 [GB] United Kingdom ............... 8609623

[51] Int. Cl.[4] .............................................. C12N 7/00
[52] U.S. Cl. ...................................... 435/235; 424/89; 424/73; 422/102; 435/284
[58] Field of Search ................ 435/1, 2, 235; 424/88, 424/89, 93

[56] References Cited

U.S. PATENT DOCUMENTS

| 3,214,340 | 9/1961 | Laurence | 435/235 |
| 4,447,537 | 1/1981 | Yunker et al. | 424/89 |
| 4,473,549 | 7/1982 | Frenkel et al. | 424/88 |

FOREIGN PATENT DOCUMENTS 0137122 8/1979 Fed. Rep. of Germany ...... 435/235

OTHER PUBLICATIONS

Nuzzolo, Tissue Culture Techniques; pp. 113–115.

Primary Examiner—Michael S. Marcus
Assistant Examiner—Lyle Alfandary-Alexander
Attorney, Agent, or Firm—Nixon & Vanderhye

[57] ABSTRACT

A method of preparing intracellular parasites for storage by infecting a layer of living cells and incubating the infected cell for 8 to 12 hours.

4 Claims, 1 Drawing Sheet

U.S. Patent  Aug. 15, 1989  4,857,463

METHOD OF PREPARING INTRACELLULAR PARASITES FOR STORAGE

This invention relates to a device and method for storing, or transporting, intracellular parasites for subsequent pathological tests or diagnosis.

It is common practice to obtain from animals, including humans, sepcimens which may contain intracellular parasites and subsequently to use those specimens for tests or diagnosis. In locations where testing or diagnostic facilities are not available it is desirable that such specimens may be taken as required and later transported to a place where diagnosis can be carried out. Additionally it is frequently desirable, as for example in patients with recurrent episodes of a disease which results from the presence of an intracellular parasite, that such specimens should be taken as soon as possible after onset of a particular episode, and at frequent intervals thereafter. The same requirement exists during an epidemiological survey, where daily sampling is desirable to determine how frequently, and for how long and to what extent, a patient is infectious. Such sampling would normally require daily visits to a doctor's surgery or a clinic, which may be difficult, so that failure to obtain the required specimens may result.

In known techniques for storing and transporting such specimens the expected life of many intracellular parasites is typically not longer than 3 or 4 days, and may be as littel as 3 to 4 hours.

It is an object of the invention to provide a device and method by means of which the foregoing difficulties are overcome and by means of which intracellular parasites may be kept viable for at least four weeks at normal temperatures, so that transport to distant locations of specimens containing these parasites may readily be effected.

The invention relies on the observation that cells which are attached to a surface and in a suitable medium will remain susceptible to infection for at least three weeks and will remain capable of synthesising an intracellular parasite to high titre following infection and treatment at a suitable temperature. The invention further relies on the observation that an infecting parasite so synthesized is extremely stable and will survive for at least a further four weeks at normal temperatures.

According to the invention there is provided a device for storing an intracellular parasite, comprising a container with an open end and having living cells attached to an inside surface thereof remote from said open end, said container being substantially filled with a buffered antibiotic and/or an antifungal liquid, and a sealable closure for said open end.

In a particular embodiment there is provided a filter device between said open end and said surface, said filter device having pores whose sizes are such as to prevent passage through the filter device of particles substantially larger than those of said intracellular parasite.

According to a further aspect of the invention there is provided a method of preparing intracellular parasites for storage or transport, comprising preparing a cell layer which is attached to a surface in a buffered antibiotic medium, adding material which includes said parasites to said medium.

Figure 2:
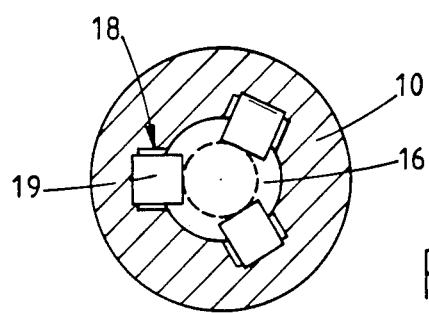

An embodiment of the invention will now be described by way of example only and with reference to the accompanying drawings in which:

FIG. 1 shows, approximately four times full size, a section through the device, and FIG. 2 is a section on line 2—2 in FIG. 1.

As shown in the drawings the device comprises a container 10 defined by two generally frusto-conical portions 11, 12 joined at their narrower ends. The larger end of the portion 11 is open and that of the portion 12 is closed to provide a base which defines an inside surface 13. Adjacent its open end the container is provided with a circumferential porjection 14 which is engageable by a resiliently deformable cap 15 which total volume of the container 10 is approximately 5 ml.

Preferably the container 10 is moulded from a suitable resilient plastics material such as polyethylene. The container 10 includes means for sealingly mounting a filter element 16 between the open end and the surface 13, the element 16 being inserted through the open end. The element 16 is a commercially available item and has through holes whose diameter is such as to limit or prevent the passage therethrough or fungi or bacteria entering the container 10 through its open end. In a particular embodiment these holes have a diameter of 500 nanometers so as to permit passage of viruses only. The element 16 is located on an internal abutment 17. Three equi-angularly spaced recesses 18 extend radially from the abutment 17 and integrally moulded resilient tabs 19 engage the element 16 to urge the latter into sealing engagement with the abutment 17. The tabs 19 are depressable into the recesses 18 to allow the element 16 to be pressed into position.

The container 10 is sterilised and filled with a suitable buffered medium 20, for example Eagle's medium, which contains antibiotic and/or antifungal agent. In the example both penicillin, streptomycin and ampheterecin are present in the buffered medium. $10^5$ cells are introduced into the medium 20 and during the next 24 hours pass down through the medium 20 to form a monolyaer 21 attached to the surface 13. The cells used are one of the known standard cell lines obtainable from the National Institute for Biological Standards and Controls, Hampstead, England and may be baby hamster kidney cells or MRC5 human embryonic lung cells. The element 16 is placed in position after the monolayer 21 has formed.

Tests have shown that if a herpes simplex virus is subsequently introduced into the medium 20, the cap 15 replaced and the container 10 and its contents subjected to a temperature between 32° C. and 37° C. for from 8 to 12 hours, the monolayer will synthesise the virus at high titre. Tests have also shown that the monolayer 21 will remain susceptible to infection by herpes simplex viruses, using the above procedure, for at least three weeks at room temperature after formation of the monolayer 21. Tests have also shown that virus synthesised in the monolayer 21 is extremely stable and will survive for at least four weeks at room temperature. If the device is maintained at a temperature between 3° C. and 7° C. after infection of the monolayer 21 as described above, the virus will survive for very much longer, and the four week viability set forth above runs from the time of its return to normal ambient temperature.

It is to be understood that though use of the device with herpes simplex viruses has been described, it is envisaged that other intracellular parasites, such as varicella-zoster virus, influenza, cytomegalovirus, enterovirus and chlamydia, and possibly also retroviruses, including the AIDS agent, could be stored by means of the device and method disclosed.

It is also to be understood that the incubation period after infection of the cell layer 21 will be adjusted as appropriate to the parasite being stored, as for example up to 3 days for varicella zoster.

In an alternative embodiment the filter 16 may be omitted and the opening between the narrower ends of the container portions 11, 12 may be made sufficiently small as to prvent a swab inserted through the upper end from reaching and disturbing the cell layer 21.

We claim:

1. A method of preparing intracellular parasites for storage comprising the steps of:
   (a) preparing a layer of living cells susceptible to infection by the parasite which cells are attached to surface in a container which is substantially filled with a buffered antibiotic medium,
   (b) adding material containing the intracellular parasites to be stored to said medium and allowing the parasites to infect the layer of living cells, and
   (c) incubating the infected cells at a temperature of between 32° C. and 37° C. for between 8 and 12 hours.

2. A method of preparing intracellular parasites for storage, comprising the steps of:
   (a) preparing a layer of living cells susceptible to infection by the parasite which cells are attached to a surface in a container which is substantially filled with a buffered antibiotic medium,
   (b) adding material containing the intracellular parasites to be stored to said medium and allowing the parasites to infect and replicate within the layer of living cells, and
   (c) incubating the infected cells at a temperature of between 32° C. and 37° C. for a time which is insufficient to result in cell lysis.

3. A method according to claim 2 in which wherein said preparing step includes introducing said cells into said medium and allowed to attach to said surface.

4. A method as claimed in claim 1 in which said cells are maintained at between 3° and 7° C. after incubation thereof.

* * * * *